(12) United States Patent
Min

(10) Patent No.: US 6,566,399 B2
(45) Date of Patent: May 20, 2003

(54) INHIBITOR OF REPLICATIVE SENESCENCE OF HUMAN KERATINOCYTES CONTAINING RETINOIC ACID AS ACTIVE INGREDIENTS

(76) Inventor: Byung-Moo Min, #13-501 Rex Apt., 300-3 Ichon-dong, Yongsan-ku, Seoul 140-030 (KR)

( * ) Notice: Subject to any disclaimer, the term of this patent is extended or adjusted under 35 U.S.C. 154(b) by 0 days.

(21) Appl. No.: 09/922,070

(22) Filed: Aug. 3, 2001

(65) Prior Publication Data

US 2002/0123526 A1 Sep. 5, 2002

(30) Foreign Application Priority Data

Aug. 3, 2000 (KR) ........................................ 2000-44972
Aug. 3, 2001 (KR) ........................................ 2001-46911

(51) Int. Cl.[7] .............................................. A01N 37/00
(52) U.S. Cl. ...................................................... 514/559
(58) Field of Search .................................. 514/725, 559

(56) References Cited

U.S. PATENT DOCUMENTS

| | | | | |
|---|---|---|---|---|
| 5,183,817 A | * | 2/1993 | Bazzano ...................... | 514/256 |
| 5,482,838 A | * | 1/1996 | West .......................... | 435/70.3 |
| 5,719,195 A | * | 2/1998 | Braiman ...................... | 514/725 |
| 6,242,435 B1 | * | 6/2001 | Achkar ....................... | 514/168 |
| 6,358,517 B1 | * | 3/2002 | Pillai et al. ................. | 424/401 |
| 6,369,100 B1 | * | 4/2002 | Nagpal et al. ............... | 514/460 |

OTHER PUBLICATIONS

Liebeskind et al, Am. J. Physiol. Cell Mol. Physiol., vol. 279, pp. 181–190, 2000.*
You et al, Biochem. Biophys. Res. Comm., vol. 268, pp. 268–274 (2000).*

Dimri, G. P., et al., "A biomarker that identifies senescent human cells in culture and in aging skin in vivo", Proc. Natl. Acad. Sci. USA, vol. 92, pp. 9363–9367, Sep. 1995.

Min, B., et al., "Terminal Differentiation of Normal Human Oral Keratinocytes Is Associated with Enhanced Cellular TGF–Beta and Phospholipase C–Gamma1 Levels and Apoptotic Cell Death", Experimental Cell Research 249, pp. 377–385, 1999.

Kang, M. K., et al., "Replicative Senescence of Normal Human Oral Keratinocytes Is Associated with the Loss of Telomerase Activity without Shortening of Telomeres", Cell Growth & Differentiation, vol. 9, pp. 85–95, Jan. 1998.

* cited by examiner

Primary Examiner—James H. Reamer
(74) Attorney, Agent, or Firm—Muserlian, Lucas and Mercanti, L.L.P.

(57) ABSTRACT

Disclosed is an inhibitor of replicative senescence of human keratinocytes containing retinoic acid, including all-trans retinoic acid, 3,4-didehydroretinoic acid, and 9-cis retinoic acid, as active ingredients. The retinoic acid plays an important role in extending the in vitro life span and inhibiting replicative senescence of the human mucosal keratinocytes and the human epidermal keratinocytes, thereby being used for a prophylactic or therapeutic agent of various diseases attributed to replicative senescence of the human oral keratinocytes. In addition, the inhibitor containing the retinoic acid can be used for a cosmetic purpose and as a prophylactic or therapeutic agent for wound-caused dermatitis and ski senescence.

3 Claims, 14 Drawing Sheets

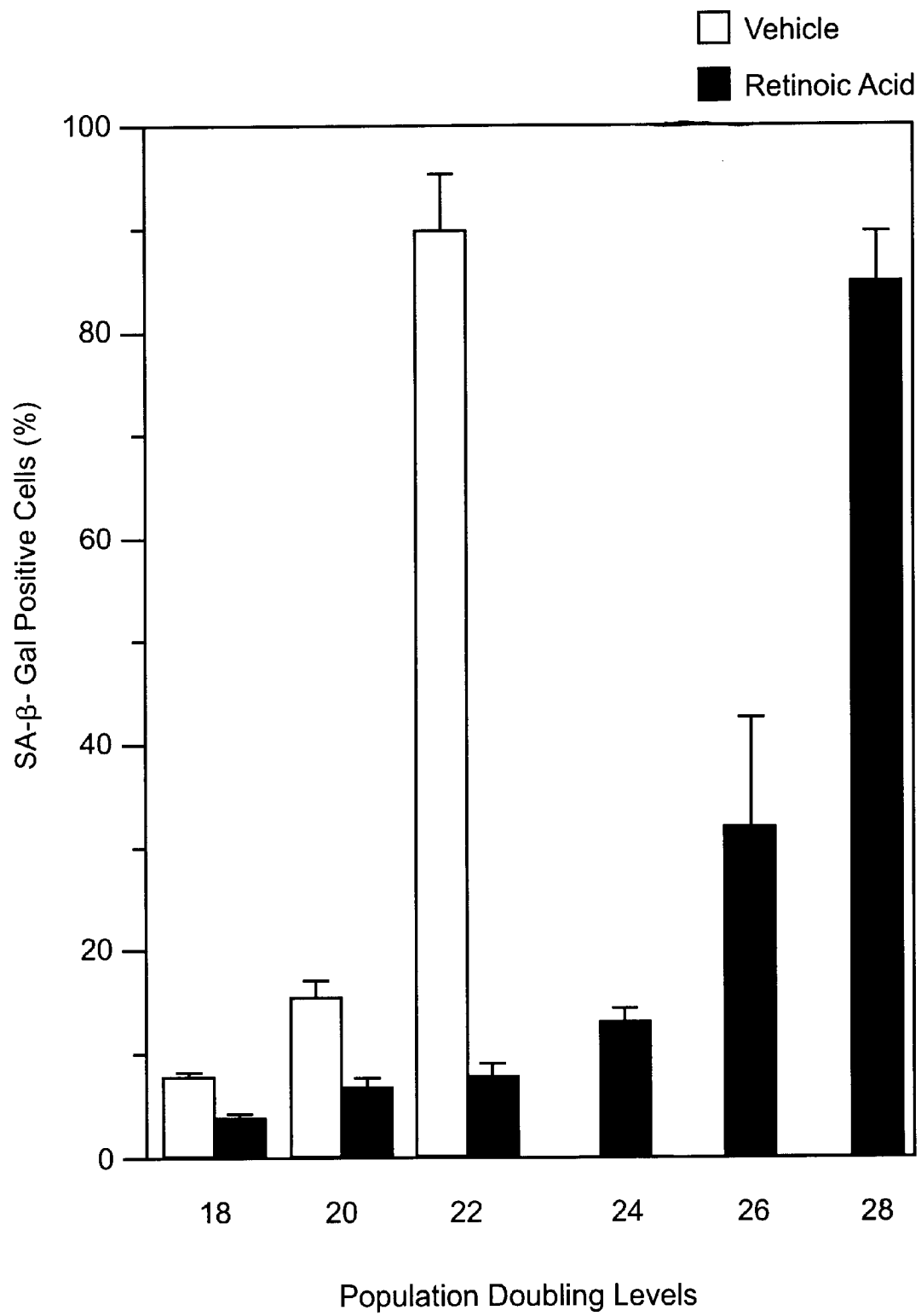

INHIBITOR OF REPLICATIVE SENESCENCE OF HUMAN KERATINOCYTES CONTAINING RETINOIC ACID AS ACTIVE INGREDIENTS

This patent application claims a benefit of priority from Korean Patent Application No. 2000-44972 filed Aug. 3, 2000 and Korean Patent Application No. 2001-46911 filed Aug. 3, 2001, the contents of each of which are incorporated herein by reference.

FIELD OF THE INVENTION

The present invention relates to an inhibitor against replicative senescence of human keratinocytes. The inhibitor against replicative senescence of human keratinocytes can extend the in vitro life span and inhibit replicative senescence. Therefore, the inhibitor containing retinoic acid as active ingredients of the present invention can be used for a prophylactic or therapeutic agent of various oral diseases, such as trauma-caused inflammation, exelcymosis-caused inflammation, burn-caused inflammation, traumatic ulcer, and angular cheilosis, for a cosmetic purpose and for a prophylactic or therapeutic agent for wound-caused dermatitis and skin senescence.

BACKGROUND OF THE INVENTION

Replicative senescence is regarded to be an essential causative element of organismic aging (Wantanabe Y. et al. *Oncogene*, 1997, 14, 2025–2032). It is assumed that such senescent cells are accumulated in the living body and the phenotype expressed from the cells alters thereby accumulating in age-related pathology (Dimri G. D., et al., *Proc. Natl. Acad. Sci.*, 1995, 92, 9363–9367).

It is shown that replicative senescence is dependent upon creative cell division, which indicates that a "mitotic clock" limits cell proliferation (Bodnor A. G. et al., *Science*, 998, 279, 349–352). It was reported that random damage caused by synthesis of RNA or protein, accumulated mutations or alternatively a genetically programmed process resulted in replicative senescence (Sugawara O. et al., *Science*, 1990, 247, 707–710).

Additionally, cell cycle regulatory proteins and tumor suppressors are known to have influence on replicative senescence. Actually, it has been certified that increased cellular levels of wild-type p53 and $p21^{WAP1/Cip1}$ proteins induce to the loss of call proliferative capacity in some cultured cells, which indicates cellular senescence (Brown J. P. et al., *Science*, 1997, 277, 831–834; Gallimore P. H et al., *Cell Growth Differ.* 1997, 8, 763–771; Sugrue M. Mm. et al., *Proc. Natl. Acad. Sci.*, 1997, 94, 9648–9653).

$p16^{INK4A}$ protein, a $G_1$ cyclin-dependent kinase (Cdk) suppressor, has also been associated with cellular senescence in a variety of cell types (Alcorta D. A. et al *Proc. Natl. Acad. Sci.*, 1996, 93, 13742–13747; Loughran O. et al., *Oncogene*, 1996, 13, 561–568; Reznikoff C. A. et al, *Cancer Res.*, 1996, 56, 2886–2890; Palmero I. et al. *Oncogene*, 1997, 15, 495–503; Uhrbom L. et al., *Oncogene* 1997, 15, 505–514). In particular, $p16^{INK4A}$ was found to form a complex with both cdk4 and cdk6 in senescent cells. Based on this result, it is believed that the regulatory phenomena, which increases intracellular $p16^{INK4A}$ protein levels, is recognized as the most important molecular change that is observed at the growth-stopped final stage of the aging process where all the growth stops. Also, the $p16^{INK4A}$ protein levels in senescent human fibroblasts are elevated compared to that of young fibroblasts, and the $p16^{INK4A}$ protein is often mutated or deleted in immortal cell lines (Vojta P. et al., *Biochem. Biophys. Acta.*, 1995, 1242, 29–41).

pRb, a tumor suppressor gene product, has also indicated the senescent state in human fibroblasts. The $p16^{INK4A}$ protein can be negatively controlled by pRb at the transcription stage. Also, it is found that neither cyclin D/cdk4 nor cyclin D/cak6 is formed in pRb-deficient cells, and thus all Cdk associate wish excessively expressed $p16^{INK4A}$ in senescent cells. This indicates that pRb is related to senescence.

Moreover, the activation of phosphatidylinositol-specific phospholipase C may also be related to cellular senescence in particular cell types (Choudhury G. G. et al., *FEBS Lett.*, 1991; 293, 211–214).

Meanwhile, the animal epithelial cells are known as have a limited proliferative capacity hang M. K. al., *Cell Growth Differ.*, 1998, 9, 85–95; Min B. -M. et al., Exp. Cell Res 1999, 249, 377–385; Dimri G. D. et al., *Proc. Natl. Acad. Sci.*, 1995, 92, 9363–9367), and thus enter the step of replicative senescence after a finite number of cell divisions.

The characteristic features of replicative senescence can be observed through culturing keratinocctes. The senescent cells stop growing, and do not enter the S phase of the ell cycle, regardless of any similar stimulation of mitogen, and inhibit levels of some genes required for cell cycling. However, the senescent cells maintain metabolic activity as usual and the ability to synthesize protein or RNA for a predetermined period of time (Dimri C-. D. et al., *Proc. Natl. Acad. Sci.*, 1995. 92, 9363–9367; Saunders N. A. et al, *Biochem. Biophy. Res. Commun.*, 1993, 197, 46–54).

Recently it is discovered that young normal human keratinocytes maintain their telomerase activity but the senescent cells lose their activity outstandingly It can be inferred from this fact that there is a positive relation between telomerase activity and replicative senescence of cells (Harle-Bachor C. et al, *Proc. Natl. Acad. Sci.* 1996, 93. 6476–6481).

The above-mentioned human epithelial cells are classified into human mucosal keratinocytes and human epidermal keratinocytes The human epithelial cells have the similar function as a protective epithelium responsible for functionally covering the skin surface. However, physically, there is a great difference. This is human epidermal keratinocytes include well-developed thick cornified cell layers, whereas the human mucosal keratinocytes have relatively thin cornified cell layers, or do not have any cornified cell layers at all (e.g., oral sulcular epithelium and junctional epithelium). In addition to differences of the physical form, human mucosal keratinocytes and human epidermal keratinocytes show a considerable difference in chemical properties and protein expression levels.

Retinoic acid, an analogue of vitamin A, plays a fundamental role in embryogenesis, reproduction, vision, and tie control of cell growth, besides other normal differentiation of many adult tissues (Sauret J. H. et al., *Horm. Res.*, 1995, 43, 89–92).

A topical administration of retinoic acid to a portion of human skin improves several aspects of photoaged skin, including fine and deep wrinkles texture, and color and it has also been found to inhibit the induction of a number of metalloproteinases involved in the destruction of the extracellular matrix (Varani J. et al., *Am. J. Pathol.* 1990, 136, 1275–1281; Varani J. et al., *J. Invest. Dermatol. Symp. Proc.*, 1998, 3, 57–60). In addition, retinoic acid also reduces the differentiation of keratinocyte, induces the deposition of glycosaminoglycan-like material in the epidermis, increases cellularity in the dermis, effects the synthesis new extracellular matrix and fibroblast activation (Varani J. et al., *Skin Pharmacol.*, 1991, 4, 254–261).

However, the effect of retinoic acid, which controls the replicative senescence of human epithelial cells on proliferation, replicative senescence, and the expression of genes, have not been reported yet.

SUMMARY OF THE INVENTION

The present invention leads to giving an intensive and thorough research of retinoic acid, which result in the finding that retinoic acid affected expression of genes and activity of proteins controlling cell proliferation and/or replicative senescence; that is a life span of both the human mucosal keratinocytes and the human epidermal keratinocytes can be extended.

Therefore, the object of the present invention is to provide an inhibitor against replicative senescence of human keratinocytes containing retinoic acid as active ingredients.

The human keratinocytes according to present invention include human mucosal keratinocytes, preferably including the human oral keratinocytes(NHOK), and human epidermal keratinocytes (NHEK).

Another object of the present invention is to provide a prophylactic or therapeutic agent of various oral diseases, such as trauma-caused inflammation, exelymosis-caused inflammation, barn-caused inflammation, traumatic ulcer, and angular cheilosis, which contains retinoic acid as active ingredients.

The object of the present invention is to provide a cosmetic purpose by containing retinoic acid as active ingredients.

It is a further object of the present invention to provide a prophylactic or therapeutic agent for wound-caused dermatitis and skin senescence, which contains retinoic acid as active ingredients.

BRIEF DESCRIPTION OF THE DRAWINGS

The above and other objects, features and other advantages of the present invention will be more clearly understood from the following detailed description taken in conjunction with the accompanying drawings, in which.

a: vehicle-treated NHOK (PDL 18)
 b: vehicle-treated NHOK (PDL 20)
 c: vehicle-treated NHOK (PDL 22)
 d: 1 nM retinoic acid-treated NHOK (PDL 18)
 e: 1 nM retinoic acid-treated NHOK (PDL 20)
 f: 1 nM retinoic acid-treated NHOK (PDL 22)
 g: 1 nM retinoic acid-treated NHOK (PDL 24)
 h: 1 nM retinoic acid-treated NHOK (PDL 26)
 i: 1 nM retinoic acid-treated NHOK (PDL 28)

Figure 3A:
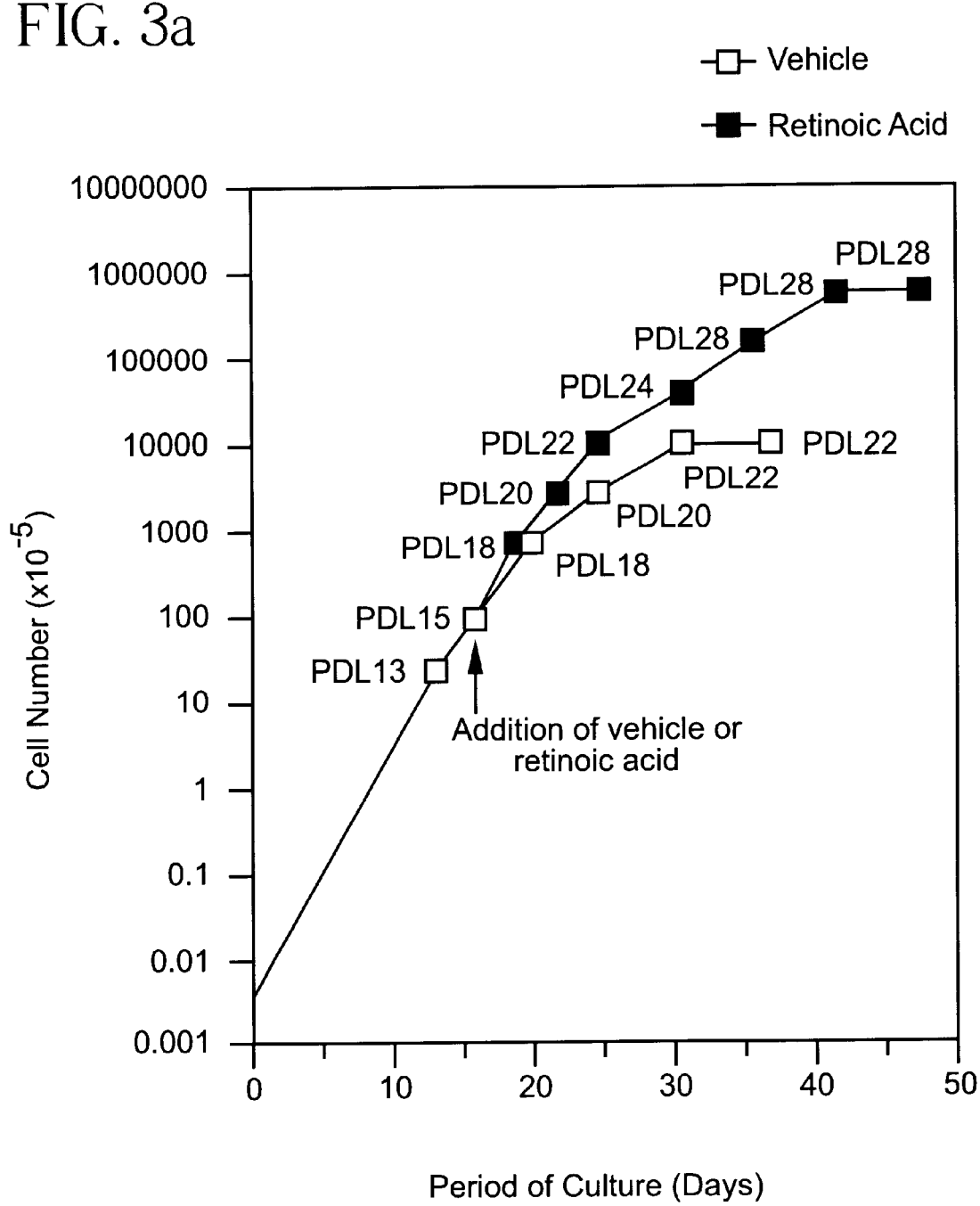
FIG. 3a is a cell growth curve showing an effect of 1 nM all-trans retinoic acid on the mitotic capacity of NHOK as PDL through continuous subculture.
Figure 3B:
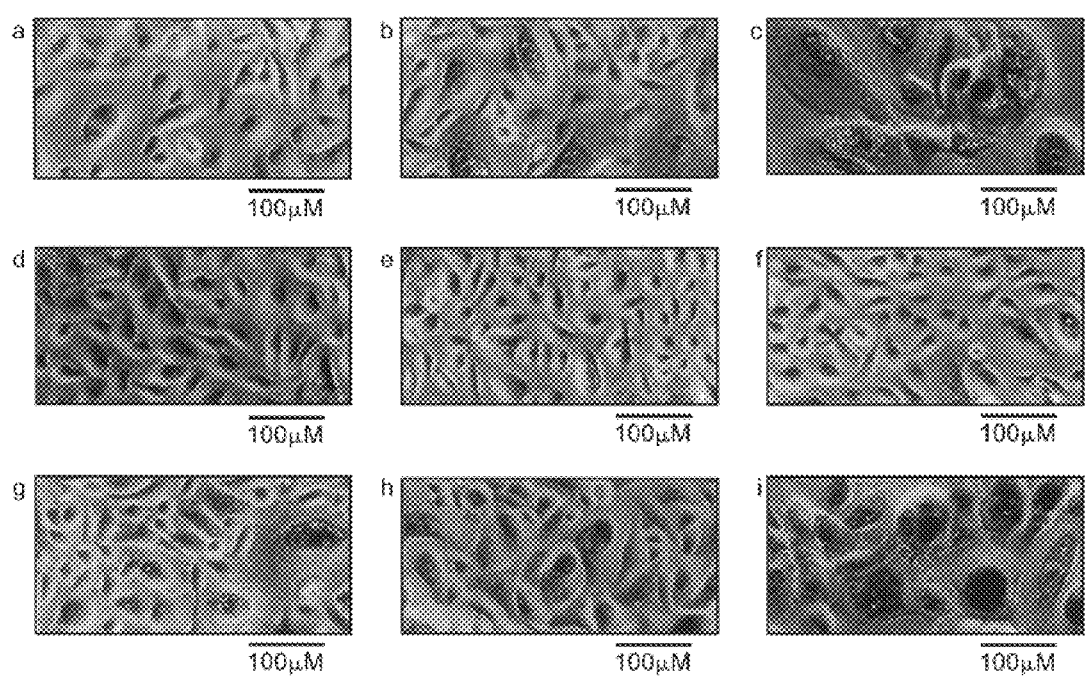
FIG. 3b shows microphotographs illustrating the extents of replicative senescence in NHOK by SA-β-gal staining after primary NHOK (PDL 15) is serially subcultured until reaching postmitotic stage in the presence of 1 nM all-trans retinoic acid.

FIG. 3c as the result of FIG. 3b is a graph showing the percentage (%) of the incidence of senescent cells using SA-β-gal staining in vehicle-treated or 1 nM all-trans retinoic acid-treated NHOK.

Figure 4A:
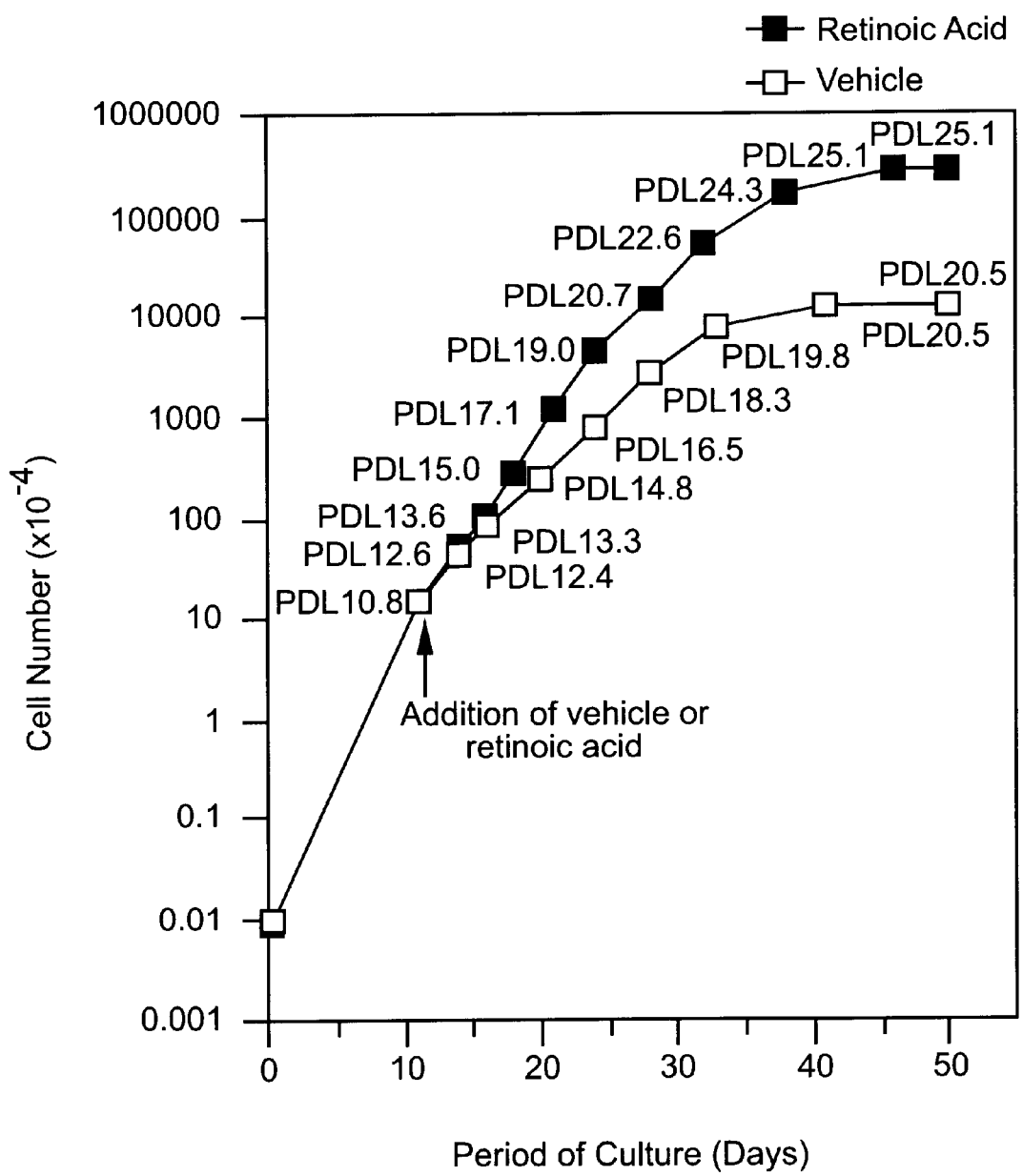

FIG. 4a is a cell growth curve showing an effect of 1 nM all-trans retinoic acid on the mitotic capacity of NHEK as PDL through continuous subculture.

Figure 4B:
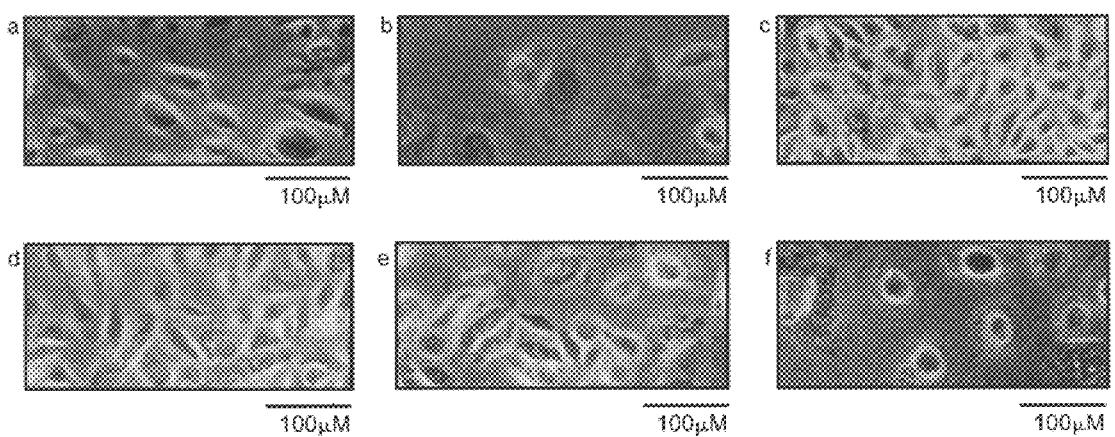

FIG. 4b shows microphotographs illustrating the extents of replicative senescence in NHEK by SA-β-gal staining after primary NHEK (PDL 10.8) is serially subcultured until reaching postmitotic stage in the presence of 1 nM all-trans retinoic acid;

a: vehicle-treated NHEK (PDT 18.3)
 b: vehicle-treated NHEK (PDL 20.5)
 c: 1 nM retinoic acid-treated NHEK (PDL 17.1)
 d: 1 nM retinoic acid-treated NHEK (PDL 20.7)
 e: 1 nM retinoic acid-treated NHEK (PDL 22.8)
 f: 1 nM retinoic acid-treated NHEK (PDL 25.1)

Figure 4C:
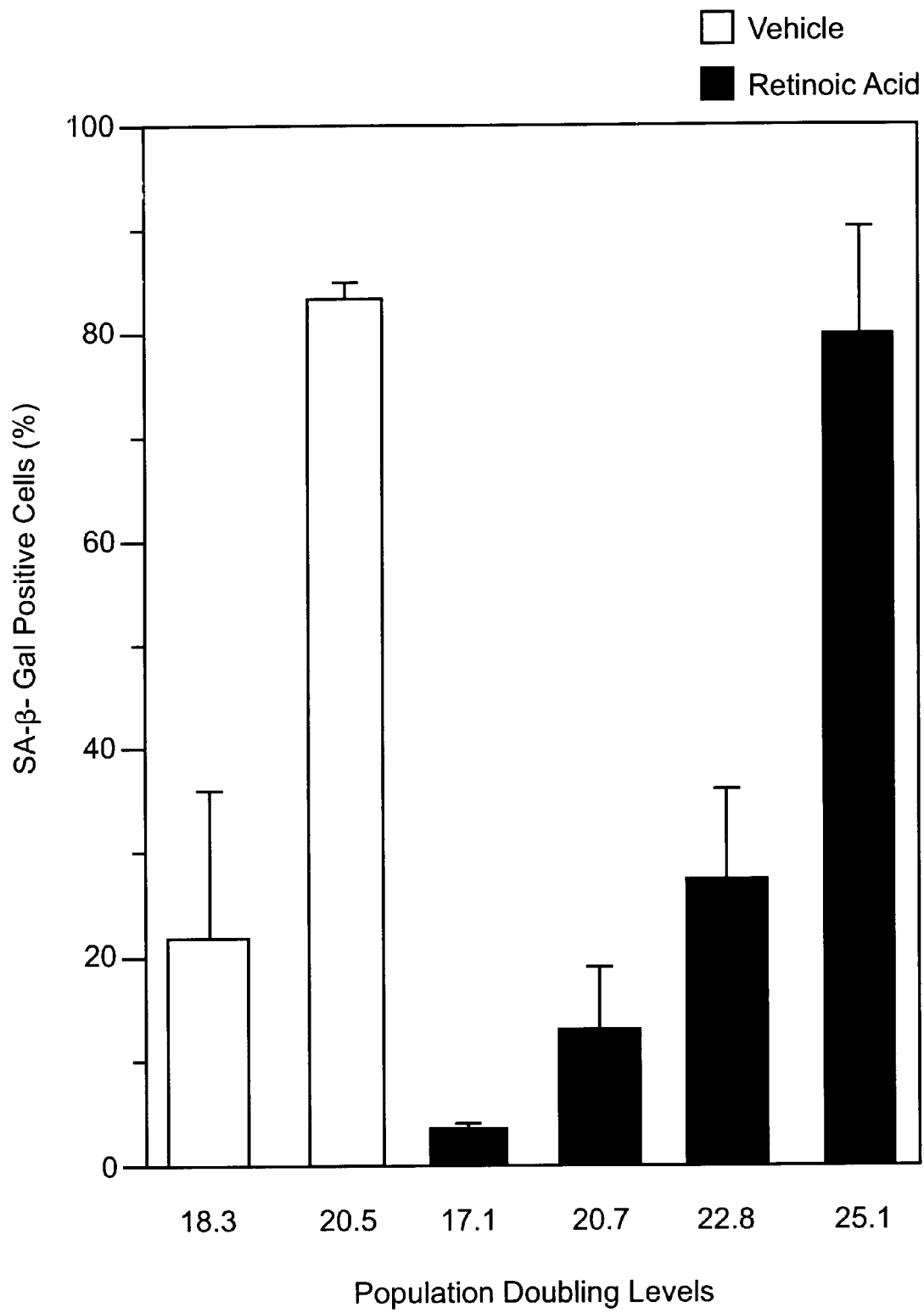

FIG. 4c as the result of FIG. 4b is a graph showing the percentage (%) of the incidence of senescent cells using SA-β-gal staining in vehicle-treated or 1 nM all-trans retinoic aid-treated NHEK.

Figure 5A:
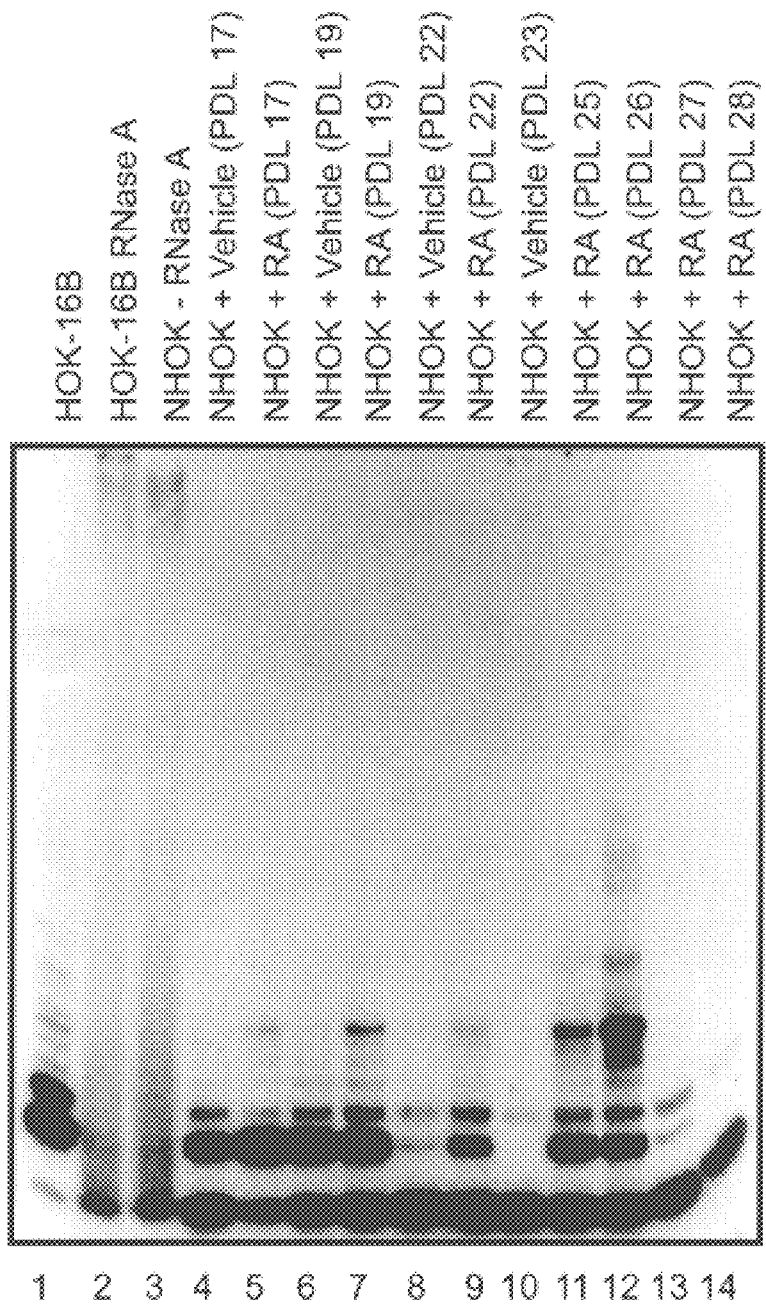

FIG. 5a shows the effect of 1 nM all-trans retinoic acid on the telomerase activity of NHOK.

Figure 5B:
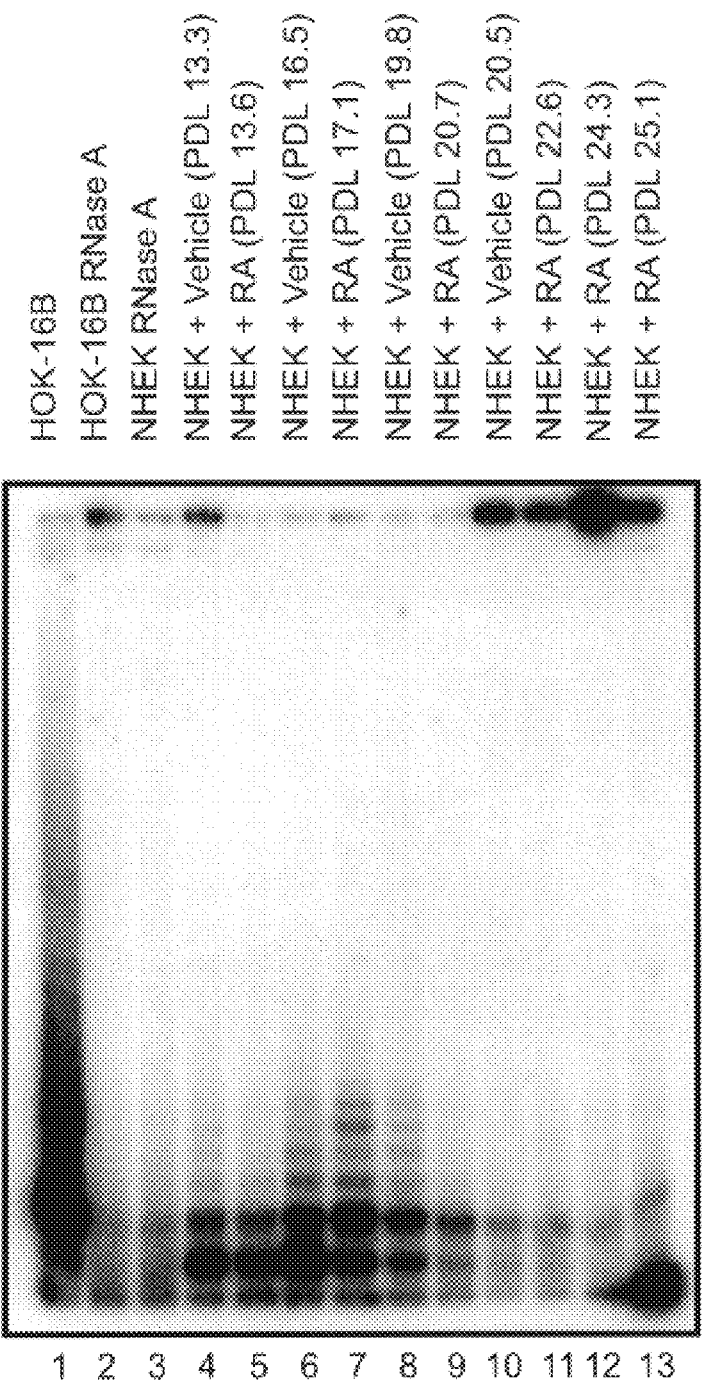

FIG. 5b shows the effect of 1 nM all-trans retinoic acid on the telomerase activity of NHEK.

Figure 6A:
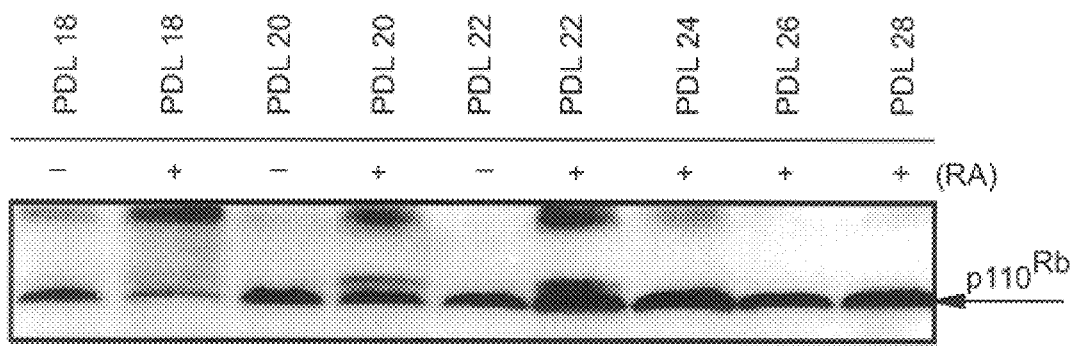

FIG. 6a shows 1 nM all-trans retinoic acid on the level of intracellular pRb protein in NHOK by Western blot analysis.

Figure 6B:
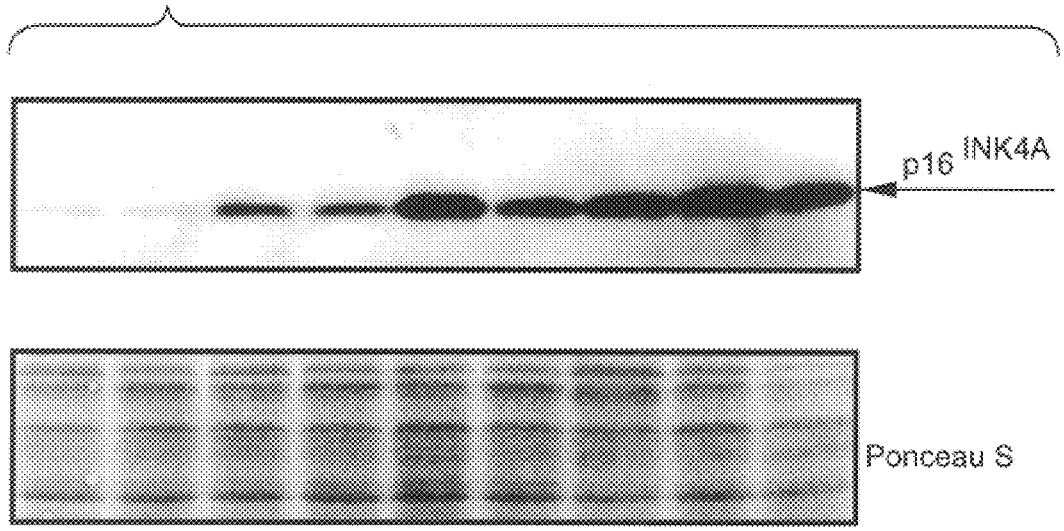

FIG. 6b shows 1 nM all-trans retinoic acid on the level of intracellular p16$^{INK4A}$ protein in NHOK by Western blot analysis.

Figure 6C:
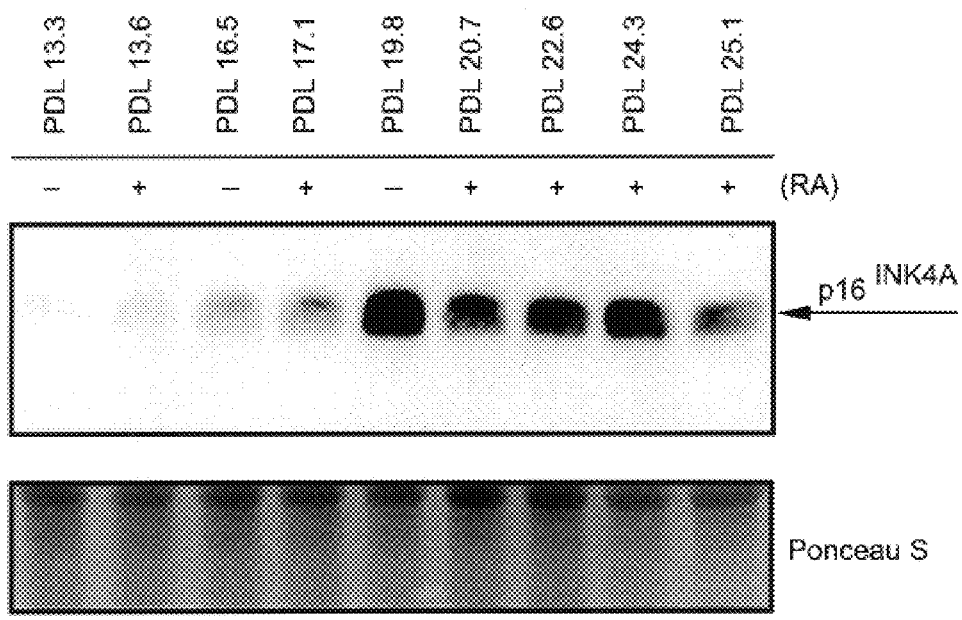

FIG. 6c shows 1 nM all-trans retinoic acid on the level of intracellular p16$^{INK4A}$ protein in NHEK by Western blot analysis.

DETAILED DESCRIPTION OF THE INVENTION

The term "Human keratinocytes", as used in the present invention, includes normal human mucosal keratinocytes and normal human epidermal keratinocytes (hereinafter, referred to as 'NHEK'). In particular, human mucosal keratinocytes may be specified to normal human oral keratinocytes (hereinafter, referred to as 'NHOK').

The present invention pertains to a retinoic acid, which is able to extend the in vitro life span of human ketatinocytes by inhibiting the cells from undergoing replicative senescence Whereby inhibiting of replicative senescence of both NHOK and NHEK and resulting in extending the in vitro life span, the inhibitor containing the retinoic acid of the present invention can be used for a prophylactic or therapeutic agent of various oral diseases, such as trauma-caused inflammation, exelcymosis-caused inflammation, burn-caused inflammation, traumatic ulcer, and angular cheilosis.

The inhibitor containing retinoic acid as active ingredients of the present invention can be used for a cosmetic purpose and for a prophylactic or therapeutic agent for wound-caused dermatitis and skin senescence.

Example of the retinoic acid in the present invention is selected from the group consisting of all-trans retinoic acid, 3,4-didehydro-retinoic acid and 9-cis retinoic acid the most preference for all-trans retinoic acid.

Figure 1A:
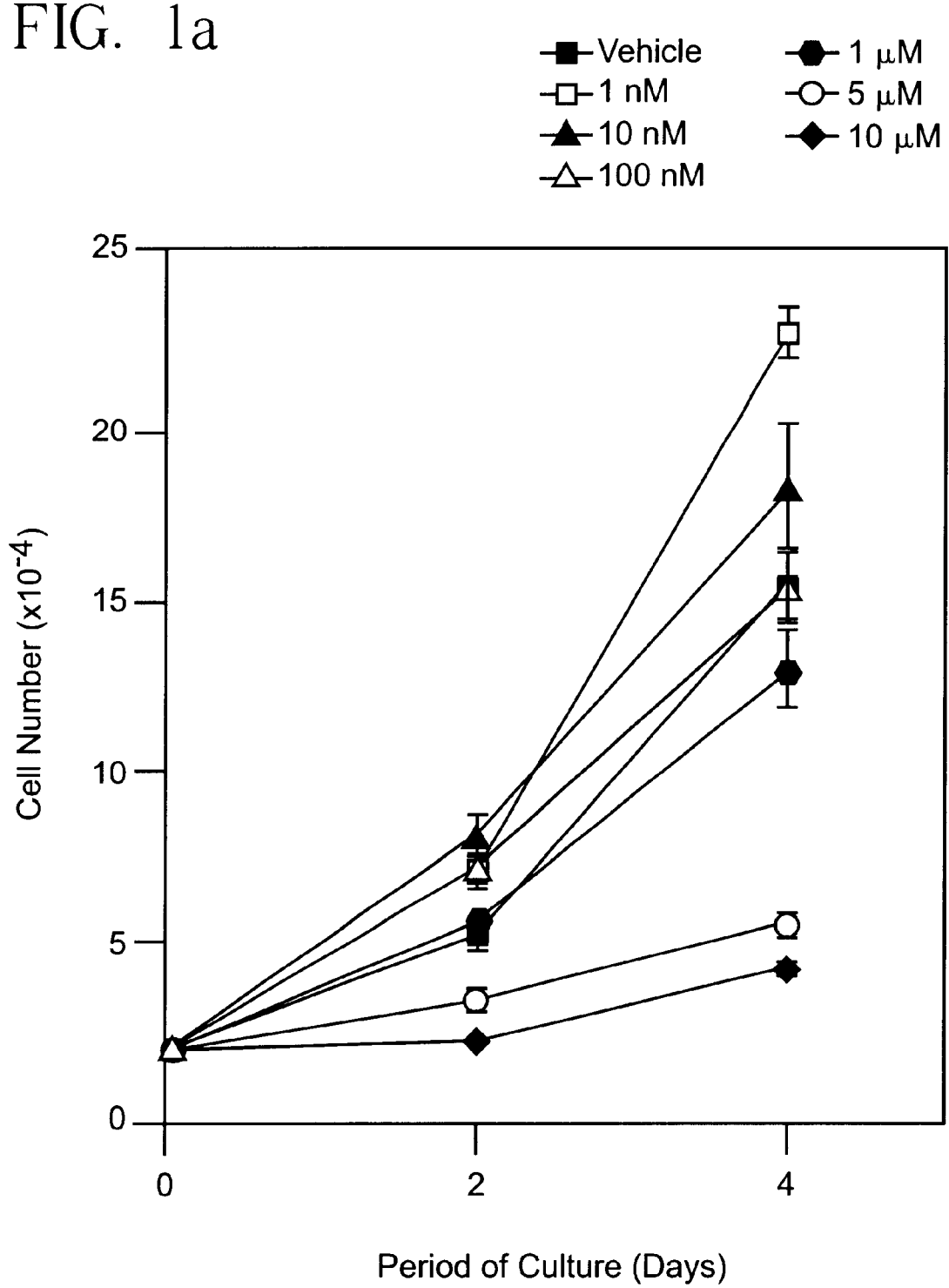
FIG. 1a is a graph showing an effect of all-trans retinoic acid on normal human oral keratinocytes (NHOK) cell numbers.
Figure 1B:
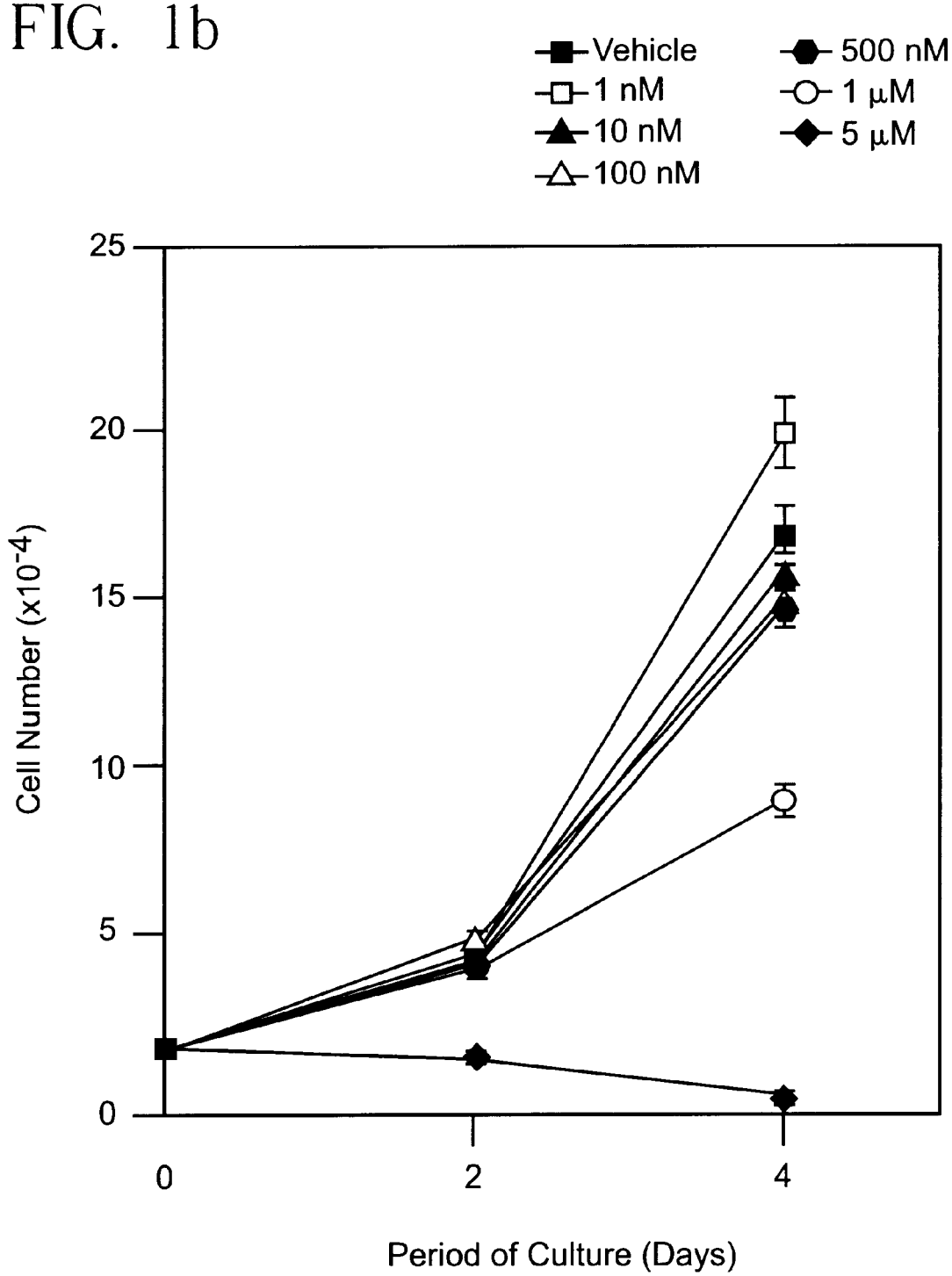
FIG. 1b is E graph showing an effect of all-trans retinoic acid on normal human epidermal keratinocytes (NHEK) cell numbers.

When rapidly proliferating NHOK and NHEK were cultured in medium containing 1 nM of retinoic acid, the in vitro life span of the cells was increased compared to vehicle control and the replicative senescence of the cells was significantly inhibited (see, FIGS. 1a and 1b).

The replicative senescence of human epithelial cells is generally associated with a steady increase of $p16^{INK4A}$ and a loss of telomerase activity.

In the present invention, it was confirmed that the retinoic acid according to present invention decreased the expression levels of pRb and $p16^{INK4A}$ proteins, and prevented the loss of the telomerase activity.

When rapidly proliferating normal cells are exposed to all-trans retinoic acid, telomerase activity is maintained or slightly increased (see, FIGS. 5a and 5b). These results indicate that the all-trans retinoic acid can prevent the loss of the telomerase activity in NHOK and NHEK, which results from repeated proliferation, and thus can inhibit replicative senescence of the cells.

The expression levels of $p16^{INK4A}$ protein in all-trans retinoic acid-treated NHOK and NHEK are notably decreased, whereby the effect of all-trans retinoic acid on replicative senescence inhibition of the cells can be inferred. In other words, all-trans retinoic acid-treated NHOK and NHEK can decrease the expression levels of $p16^{INK4A}$ protein in cells to extend the in vitro life span. Additionally, at low population doubling levels (PDL), all-trans retinoic acid-treated cells have noticeably lower pRb protein levels than a vehicle control having corresponding PDL. On the other hand, at high PDL, the all-trans retinoic acid-treated cells have higher pRb protein levels compared to those of the vehicle control. Therefore, the inhibitor containing the retinoic acid as active ingredients of the present invention can present the expression levels of $p16^{INK4A}$ protein in NHOK and NHEK, and maintain telomerase activity in the face of continuous proliferation, thereby inhibiting against replicative senescence of both NHOK and NHEK. With these effects, the inhibitor containing the retinoic acid of the present invention can be used as a prophylactic or therapeutic agent of various oral and epidermal diseases attributed to replicative senescence of the human keratinocytes.

Administrable via oral or parenteral routes, she retinoic acid of he present invention may be used with ordinary medicine forms. In particular, parenteral injectable solution is preferable. That is, the retinoic acid of the present invention can be formulated into various dosage forms for oral or parenteral administration. For formulation, pharmaceutically acceptable diluents, expedients and/or carriers may be used, including fillers, thickeners, binders, wetting agents, disintegrants, surfactants etc. Tablets, pills, powders, granules, and capsules exemplify solid dosage form for oral administration. These solid forms are prepared by mixing at least one retinoic acid with at least one expedient, such as starch calcium carbonate, sucrose, lactose, gelatine, etc. In addition to expedients, a lubricant such as magnesium styrate lazy be added.

Exemplified by suspensions, internal solutions, emulsion, syrups, etc., liquid dosage forms oral administration may comprise simple diluents, such as water and liquid paraffin, as well as wetting agents, sweeteners, aromatics, and/or perspectives.

Dosage forms for parenteral administration including subcutaneous, intravenous, or intramuscular introduction are formulated ample or vial unit that are prepared to sterile aqueous solution mixing stabilizer or buffer with water or emulsions.

Typical daily doses may range from 100 to 2000 mg/kg body weight to adult, more preferably 100 to 1000 mg/kg body weight and they can be administered in a single dose or in divided doses. The dosage may vary depending on the subject, including, for example, physical constitutions and weights of patients, kinds, and severity of disease, administration routes and intervals, etc.

A better understanding of the present invention may be obtained in light of the following examples which are set forth to illustrate but are not to be construed to limit the present invention.

EXAMPLE 1

Measurement of NHOK Proliferation Rate with All-trans Retinoic Acid

Step 1: Culture of primary NHOK

NHOK were prepared from human gingival tissue specimens (Min B. -M. et al., *Int. J. Oncol.*, 1395, 7, 249–256). The tissue samples obtained from four healthy volunteers (ages ranged from 18 to 30 years) were thoroughly washed three times with calcium and magnesium-free Hanks' balanced salt solution (CMF-HBSS; GibcoBRL). In order to separate the epithelial tissue from the underlying mucosa, the tissue scruples were incubated in CMF-HBSS containing collagenase type II (1.0 mg/ml; Sigma Chemical Co.) and dispase grade II (2.4 mg/ml; Boeringer-Mannheim) for 90 min at 37° C. in 95% air and 5% carbon dioxide Primary NHOK were prepared from separated oral epithelial tissue (Min B. -M. et al., *Int. J. Oncol.* 1995, 7, 249–256), and cultured in keratinocyte basal medium containing 0.15 mM calcium and supplementary growth factor bullet kit (KGM; Clonetics Corp.) as described above. Approximately 70% confluent primary NHOK were plated at $1\times10^5$ cells per 60 mm petri dish, cultured until the cells reached 70% confluency, and then subcultured at every 70% confluency until they reached the postmitotic stage of cell proliferation. At the end of each passage, $1\times10^6$ and $3\times10^6$ NHOK were washed with 1X phosphate-buffered saline (PBS). The separated cell pellets were stored at −70° C. for TRAP and Western blot analysis.

The HOK-16B cells: human oral keratinocytes immortalized by transfection with cloned human papillomavirus type of genome (Park N. H. et al., *Carcinogenesis*, 1991, 12, 1627–1631, were also cultured in KGM and used as a control in the following example 2.

As mentioned above, primary NHOK separated from gingival epithelial tissue were aliquoted to 60-mm petri dishes. Three days after cell seeding, the number of cells that were originally plated was determined by cell colony counting. Cells were cultured until they reached 70% confluency, at which time the cell numbers from three different dishes were countered using a hemocytometer to determine the number of PDLs of the primary NHOK cultures.

Harvested primary cultures were subcultured until they reached the postmitotic stage of cell proliferation.

At the end of each stage, the population doubling level of NHOK was calculated by the following equation 1:

Equation 1

$$2^N = C_f/C_i$$

Wherein, N: PDL, $C_f$: total cell numbers obtained from the end of a passage, $C_i$: total cell numbers of attached cells at seeding.

Step 2: Measurement of NHOK proliferation rate with all-trans retinoic acid

To determine the effect of all-trans retinoic acid on cell proliferation, rapidly proliferating NHOK (PDL 18) were plated at $2\times10^4$ cells per well in a 24-well culture plate. When the cultures reached 40% confluency (24 hours after the plating), cells were exposed to all-trans retinoic acid of various concentrations from 1 nM to 10 μM (1 nM, 10 nM, 100 nM, 1 μM, 5 μM, and 10 μM) and harvested after 2 or 4 days of incubation to count the number of viable cells by trypan blue exclusion. The average number and standard deviation were calculated as the means of four independent experiments (FIG. 1a).

Referring to FIG. 1a, there is shown a graph illustrating the effect of all-trans retinoic acid on proliferation of NHOK. As seen in the growth curve, NHOK exposed to 1 or 10 nM all-trans retinoic acid were noticeably increased in cell proliferation compared to the vehicle control 1 nM of all-trans retinoic acid in the test concentrations used maximally enhanced cell proliferation of NHOK.

EXAMPLE 2

Measurement of NHEK Proliferation Rate with All-Trans Retinoic Acid

Step 1: Culture of Primary NHEK

NHEK was prepared in the same manner as in the above example 1, except that tissue samples were taken from human foreskin tissue specimens of two healthy volunteers (ages ranged from 1 to 3 years).

Step 2: Measurement of NHEK proliferation with all-trans retinoic acid

To determine the effect of all-trans retinoic acid on cell proliferation, rapidly proliferating NHEK (PDL 11) were plated at $2\times10^4$ cell per well in a 24-well plate and cultured until their cell density reached 40% (24 hours after the plating). The cultured cells were exposed to all-trans retinoic acid containing various concentrations, 1 nM, 10 nM, 100 nM, 500 nM, 1 μM, and 5 μM and harvested after 2 or 4 days of incubation to count the number of viable cells by trypan blue exclusion. The average number and standard deviation was calculated as above same procedure (FIG. 1b).

With reference to FIG. 1b, there is shown graph illustrating the effect of retinoic acid on proliferation of NHEK. As seen, NHEK exposed to 1 nM all-trans retinoic acid were notably increased in cell proliferation, compared to the vehicle control. The maximum cell proliferation was observed from the cell exposed to 1 nM all-trans retinoic acid. However, the cells exposed to all-trans retinoic acid of 1 μM, or higher were restrained in their growth.

EXAMPLE 3

Measurement of Senescence Inhibition of NHOK by All-trans Retinoic Acid

The senescent NHOK were positively stained by β-galactosidase (Dimri G. D. et al., Proc. Nat. Acad. Sci., 1995, 92, 9363–9367). Using such properties, the inhibition against senescence of all-trans retinoic acid-treated NHOK was examined. As described in the above example 1, the cultured NHOK were plated to 35-mm petri dish, cultured, and washed with 1X PBS, after which NHOK was immobilized with PBS containing 2% formaldehyde and 0.2% glutaraldehyde and then washed with PBS supplemented with 1 MM $MgCl_2$ The cells were allowed to stand in 1 mg/ml of 5-bromo-4-chloro-3-indolyl β-D-galactoside (X-Cal; Promega Corp.)—containing SA-β-gal staining solution [composition 150 mM, NaCl, 2 mM $MgCl_2$, 5 mM potassium ferrocyanide, 5 mM potassium ferricyanide, 40 mM citric acid, 12 mM sodium phosphate, pH 6.0] at 37° C. and stained overnight.

To ensure a representative count, each cell culture was divided into four equal parts and minimum two areas per each part were photographed with Olympus IMT-2 phase-contrast microscope, thus counting the cells. As the result, minimum 500 or more cells per each part were counted.

After the senescent NHOK (PDL 22) were exposed to 1, 10, or 100 nM retinoic acid for 21 days the percentage (%) of senescent cells was obtained from SA-β-gal positive cell (%) versus total cells. The average percentage (%) and standard deviation were calculated from three independent experiments.

Figure 2A:
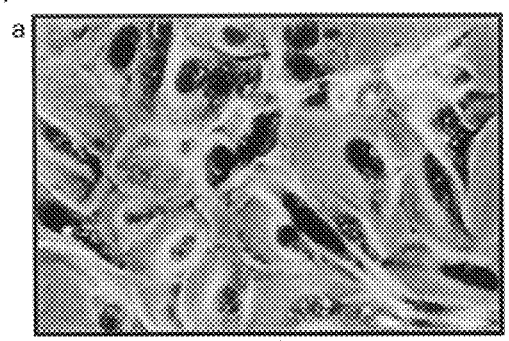
FIG. 2a shows microphotographs of replicative senescence of senescent NHOK (PDL 22) by SA-β-gal staining, which the cells are cultured with a variety of concentrations of the all-trans retinoic acid;
 a; vehicle control
 b; 1 nM all-trans retinoic acid
 c; 10 nM all-trans retinoic acid
 d; 100 nM all-trans retinoic acid FIG. 2b as the result of FIG. 2a is a graph showing the percentage (%) of SA-β-gal positive cells in the total cell count.
Figure 2A:
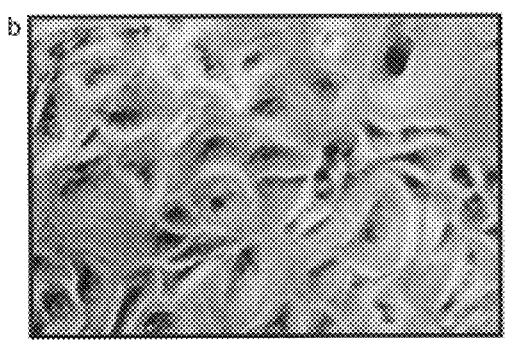
Figure 2A:
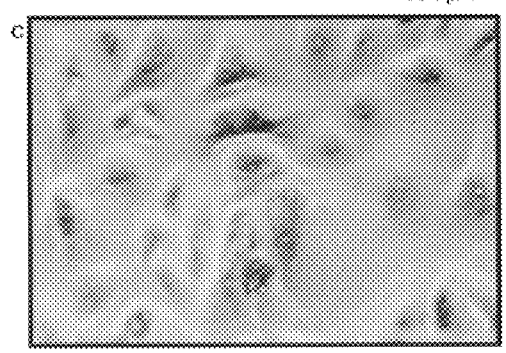
Figure 2A:
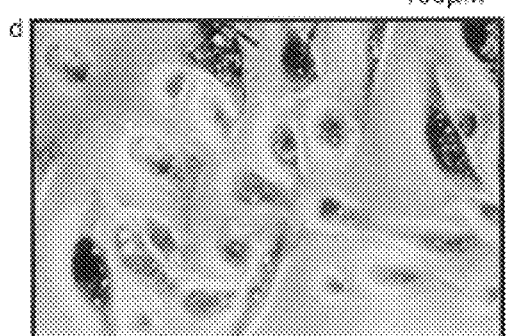
Figure 2B:
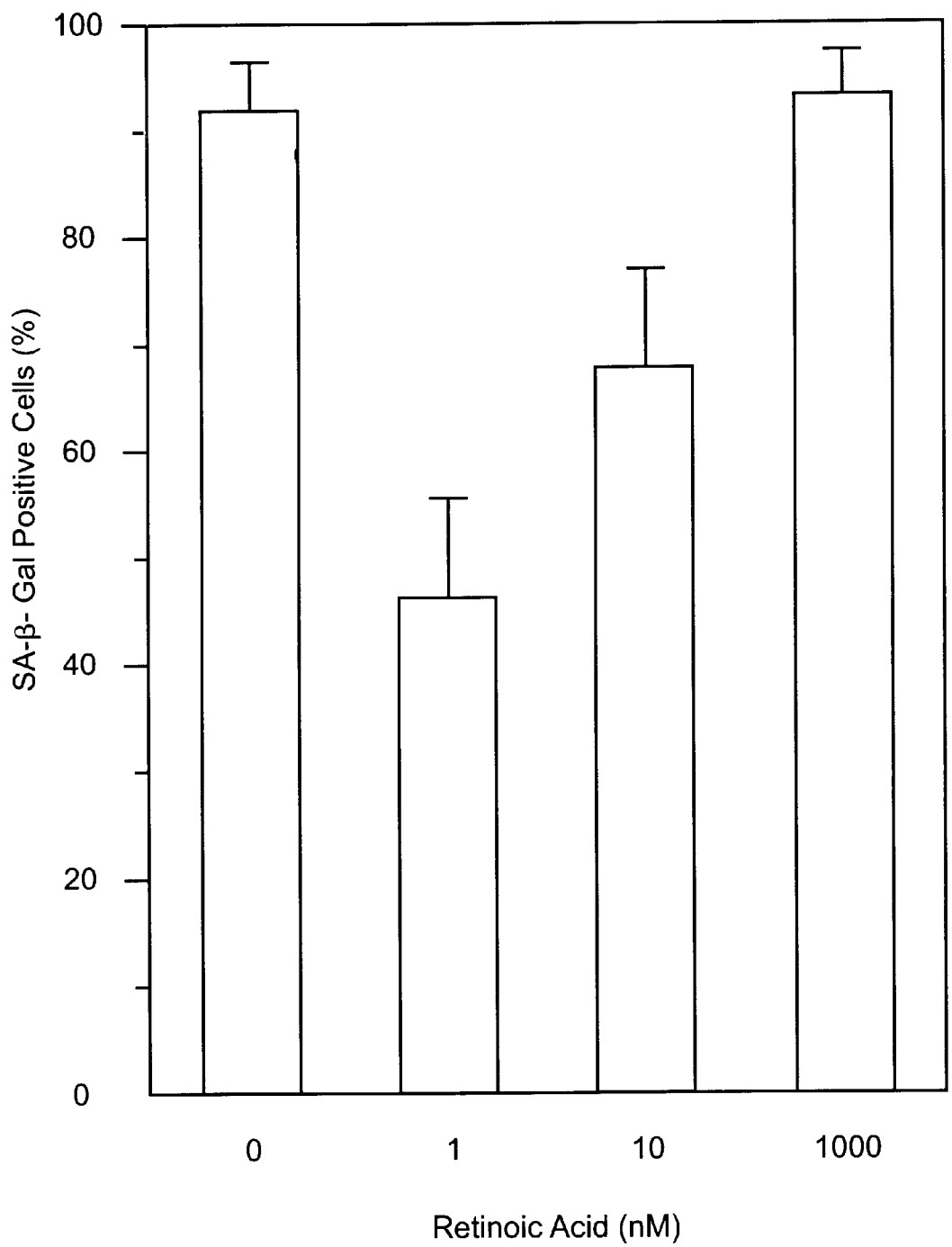

FIG. 2a shows microphotographs of the replicative senescence-generated NHOK at PDL 22 by SA-β-gal staining. The cells are exposed to all-trans retinoic acid of various concentrations, in which the concentrations of the all-trans retinoic acid are a: vehicle control, b: 1 nM all-trans retinoic acid, c: 10 nM all-trans retinoic acid, and d: 100 nM all-trans retinoic acid. FIG. 2b, showing the result of FIG. 2a, depicts a graph showing the percentage (%) of relative senescence-generated NHOK (PDL 22) versus total cells, in which the cells exposed to 1 nM all-trans retinoic acid were considerably affected the inhibition undergoing replicative senescence, compared to the vehicle control.

From the results of FIGS. 2a and 2b, at found that the replicative senescence in senescent cells exposed to 1 nM of all-trans retinoic acid was significantly inhibited compared to that of the vehicle control. That is, 1 nM of all-trans retinoic acid-treated NHOK maximally, enhanced cell proliferation and inhibited replicative senescence.

EXAMPLE 4

Effect of All-trans Retinoic Acid on Mitotic Capacity of NHOK and NHEK

The mitotic capacity of the cells exposed to all-trans retinoic acid was measured and the effect of all-trans retinoic acid of both NHOK and NHEK was investigated according to the following procedures.

NOOK (PDL 15) showing rapid proliferation was cultured with $2\times10^5$ cell per 60-mm petri dish. In addition, NHEK (PDL 11) was cultured in the same manner as in the NHOK. The cells were divided into two groups, which were cultured in KGM containing vehicle (0.001% DMSO) or 1 nM all-trans retinoic acid until the cells reached 70% confluency, and then subcultured until they reached the postmitotic stage of cell proliferation. All-trans retinoic acid was used by dissolving it in DMSO and then diluting with KGM so as to have a final DMSO concentration of 0.001%. The PDL accumulated at the last stage of each subculture and the senescent cell numbers in the cultured NHOK and NHEK, that is to say, the percentage (%) of positive cells by SA-β-gal staining were determined. The cell pellet obtained after washing with 1X PBS was frozen at −70° C. for TRAP and Western blot analysis (see, FIGS. 3a, 3b, 3c, 4a, 4b, and 4c).

FIG. 3a shows a cell growth curve showing the effect of 1 nM all-trans retinoic acid on the mitotic capacity of NHOK as PDL through continuous subculture, and FIG. 3b shows microphotographs illustrating the extent of replicative senescence by SA-β-gal staining after rapidly proliferating NHOK (PDL 15) were cultured until reaching postmitotic stage in the presence of 1 nM all-trans retinoic acid. In this figure, a designates NHOK (PDL 18) treated with vehicle; b, NHOK (PDL 20) treated with vehicle; c, NHOK (PDL 22) treated with vehicle; d, NHOK (PDL 18) treated with 1 nM retinoic acid; e, NHOK (PDL 20) treated with 1 nM retinoic acid; f, NHOK (PDL 22) treated with 1 nM retinoic acid; g, NHOK (PDL 24) treated with 1 nM retinoic acid; h, NHOK (PDL 26) treated with 1 nM retinoic acid; and i, NHOK (PDL 28) treated with 1 nM retinoic acid FIG. 3c, showing the result of FIG. 3b. depicts the percentage (%) of senescent cells versus total cells.

From the results of FIGS. 3a, 3b, and 3c, which snow cell division of NHOK, it can be seen that NHOK (PDL 15) exposed to vehicle proliferated well until PDL 20, which constituted the log phase of the cell growth curve. Some of NHOK cells show replicative senescence at PDL 20. At PDL 22, most cells show the positive reaction for SA-β-gal staining which was characteristic of replicative senescence, and their growth was stopped. However, in 1 nM all-trans retinoic acid-treated NHOK, the log phase of cell proliferation was observed from PDL 0 to PDL 26, and these cells apparently ceased to proliferate at PDL 28.

FIG. 4a shows a cell growth curve showing the effect of 1 nM all-trans retinoic aced on the mitotic capacity of NHEK as PDL through continuous subculture. FIG. 4b shows microphotographs illustrating the extent of replicative senescence by SA-β-gal staining after rapidly proliferating NHEK (PDL 10.8) are cultured until reaching post-mitotic stage in the presence of 1 nM all-trans retinoic acid, in which a designates NHEK (PDL 18.3) treated with vehicle; b, NHEK (PDL 20.5) treated with vehicle; c, NHEK (PDL 17.1) treated 1 nM retinoic acid; d, NHEK (PDL 20.7) treated with 1 mM retinoic acid; e, NHEK (PDL 22.8) treated with 1 nM, retinoic acid; f, NHEK (PDL 25.1) treated with 1 nM retinoic acid. FIG. 4c depicts the percentage (%) of senescent cells versus total cells.

From the results of FIGS. 4a, 4b, and 4c which show cell division of NHEK, it can be seen that NHEK (PDL 10.8) treated with vehicle as the negative control proliferates well until the PDL reaches 19.8, which corresponds to log phase of the cell growth curve. Some of NHEK cells show replicative senescence at PDL 18.3 At PDL 20.5, most cells showed positive reaction for SA-β-gal staining, which was characteristic of replicative senescence, and their growth was ceased. However, in NHEK cultures exposed to 1 nM all-trans retinoic acid, the log phase of cell proliferation was observed from PDL 0 to PDL 24.3, and these cells did not further proliferate following proliferation up to PDL 25.1. According to these results, 1 nM of all-trans retinoic acid-treated cells improved the effect on inhibition against replicative senescence and then increased cell proliferation, thereby, 1 nM of all-trans retinoic acid in present invention was recognized to be inhibit against replicative senescence through the result the log phages of cell proliferation.

EXAMPLE 5

Effect of All-trans Retinoic Acid on Telomerase Activity of NHOK and NHEK

To investigate telomerase activity of NHOK and NHEK exposed to all-trans retinoic acid, the telomerase activity was determined using a TPAP-eze telomerase detection kit (Oncor Inc.), which, is based on the TRAP assay.

More specifically, the frozen cell pellet in the above example 4 was dissolved in 200 μl of 1X CHAPS buffer (composition: 10 mM Tris-HCl pH 7.5, 1 mM MgCl$_2$; 1 mM EDTA 0.5% 3[(3-cholamidopropyl)-dimethylammonium]-1-propanesulfonate, 10% glycerol, 5 mM β-mercaptoethanol and 0.1 mM benzamidine), incubated on ice for 30 minutes; and then centrifuged at 12,000 rpm for 30 minutes at 4° C. The separated supernatant was aliquoted and frozen on dry ice for TRAP assay. The protein concentration of the supernatant was determined using a Bio-Rad protein assay reagent, supplied from Bio-Rad Co. HOK-16B cell lysate having telomerase activity was used as a positive control cell extract, and HOK-16B extract treated with 200 μg/ml Rnase A (Sigma Chemical Co.) as a negative control.

For TRAP analysis, 2 μl of cell lysate containing 1.0 μg of cellular proteins were added to 48 μl of solution including 1X TRAP reaction buffer [composition: 20 mM Tris-HCl (pH 8.3), 1.5 mM MgCl$_2$, 63 mM KCl 0.005% Tween 20, and 1 mM EGTA], 50 μM of each of four types of deoxynucleotide triphosphates, 0.05 μg of TS primer end-labeled with 20 μCi of [$\gamma^{32}$-P] ATP (3000 Ci/mmol; Amersham Corp.), 1 μl of primer mix, and Taq DNA polymerase (Perkin-Elmer) 0.4 unity. The prepared reaction mixture was incubated for 30 minutes at 30° C., and the telomerase reaction product amplified using a DNA thermal cycler (Perkin-Elmer). The following conditions were used for the PCR cycle: 30 cycles at 94° C. for 30 seconds and 55° C. for 30 seconds, followed by one delayed extension cycle for 10 minutes at 72° C. The PCR products were run in 12.5% nondenaturing polyacrylamide gel in 1X Tris-borate EDTA for 90 minutes at 60 W. After drying the gel, the radioactive signal was detected by autoradiography.

FIG. 5a shows the telomerase activity of NHOK exposed to 1 nM all-trans retinoic acid and the vehicle control, analyzed through TRAP assay techniques. From the result, the cell extracts (lanes 4, 6, and 8 in FIG. 5a) obtained from the vehicle-treated NHOK cultures at PDL 17, 19, and 22, and from the all-trans retinoic acid-treated cells at PDL 17, 19, 22, 25, and 26 (lanes 5, 7, 9, 11, and 12 in FIG. 5a) can be seen the telomerase activity.

The telomerase activity in the vehicle control with different PDL numbers were similar; however, the telomerase activity was maintained or slightly increased in the retinoic acid-treated NHOK at high PDL numbers. In addition, telomerase activity in vehicle-treated NHOK at PDL 23 and all-trans retinoic acid-treated cells at PDL 27 and 28, showing the characteristic of replicative senescence was almost undetectable (lanes 10, 13, and 14 in FIG. 5a), compared to cell extracts obtained from rapidly proliferating NHOK.

FIG. 5b illustrates the telomerase activity of NHEK exposed to 1 nM all-trans retinoic acid and the vehicle control, analyzed through TRAP assay techniques. As can be seen in the above drawing, the cell extracts (lanes 4, 6, and 8 In FIG. 5b) obtained from the vehicle-treated NHEK cultures at PDL 13.3, 16.5, and 19.8, and the cell extracts (lanes 5, 7, 9, and 11. in FIG. 5b) obtained from the all-trans retinoic acid-treated cells at PDL 13.6, 17.1, 20.7, and 22.6 have telomerase activity. In the vehicle-treated NHEK, telomerase activity was similar, regardless of PDL. However, in the all-trans retinoic acid-treated NHEK experimental group, telomerase activity was maintained according to the increase of PDL. Also, telomerase activity in vehicle-treated NHEK at PDL 20.5 and in all-trans retinoic acid-treated cells at PDL 24.3 and 25.1, showing the characteristic of replicative senescence, was hardly or almost undetected (lanes 10, 12, and 13 in FIG. 5b), compared to the cell extracts from rapidly proliferating NHEK.

Therefore, from the results of FIGS. 5a and 5b. it can be confirmed that, when rapidly proliferating NHOK and NHEK, are exposed to 1 nM all-trans retinoic acid, telomerase activity is maintained or slightly increased. The all-trans retinoic acid can prevent the loss of telomerase activity in NHOK and NHEK attributed to repeated proliferation, thus inhibiting replicative senescence of the cells.

EXAMPLE 6

Effect of All-trans Retinoic Acid on $p16^{INK4A}$ Protein Level in NHOK and NHEK To investigate the expression levels of pRb and $p16^{INK4A}$ proteins in NHOK and NHEK that are exposed to all trans retinoic acid, Western blot analysis (Min B. -M. et al., *Int. J. Oncol.*, 1995, 7, 249–256) was performed using anti-mouse Rb (IFB) monoclonal antibody and anti-human p16 (C-20) polyclonal antibody (Santa Cruz Biotechnology). After probing with each of the respective antibodies, the membrane was stained with 1X Ponceau S stain for 10 minutes to reveal the total protein loading per lane.

FIG. 6a shows the pRb protein level in 1 nM all-trans retinoic acid-treated NHOK, which is measured by Western blot analysis. The pRb protein level of NHOK in vehicle control was found to be similar with other PDL numbers, However, in all-trans retinoic acid-treated NHOK, the amount of pRb protein was extremely low in the early culture at PDL 18 and gradually increased in the cells at high PDL numbers. At low PDL, all-trans retinoic acid-treated NHOK had much lower pRb protein levels than the vehicle control corresponding PDL, but had higher levels according to the increase of PDL.

FIG. 6b shows the intracellular $p16^{INK4A}$ protein level in NHOK determined through Western blot analysis. The intracellular $p16^{INK4A}$ protein level in all-trans retinoic acid-treated oral keratinocytes was significantly lower than that of the vehicle control at any given number. From this result, all-trans retinoic acid induces the in vitro life span extension of oral keratinocytes by decreasing the intracellular $p16^{INK4A}$ protein level.

Therefore, the level of intracellular $p16^{INK4A}$ protein was gradually and significantly enhanced in calls with increased PDL numbers exposed to both vehicle and 1 nM of all-trans retinoic acid.

The intracellular $p16^{INK4A}$ protein level confirmed from senescent cells of the all-trans retinoic acid-treated NHOK at PDL 28 was similar to vehicle-treated control, but all-trans retinoic acid-treated NHOK having lower PDL had notably decreased. This means that all-trans retinoic acid maintains telomerase activity in NHOK and induces the in vitro life span extension of the human oral keratinocytes by decreasing the intracellular $p16^{INK4A}$ protein level.

FIG. 6c shows the intracellular $p16^{INK4A}$ protein level in 1 nM all-trans retinoic acid-treated NHEK, which was determined by Western blot analysis. According to the increase of PDL intracellular $p16^{INK4A}$ protein levels were gradually increased in both all-trans retinoic acid-treated NHEK and vehicle-treated NHEK. The intracellular $p16^{INK4A}$ protein levels confirmed that the senescent cells of all-trans retinoic acid-treated NHEK at PDL 24.3–25.1 was similar to vehicle-treated control but all-trans retinoic acid-treated NHEK at PDL 13.6–17.1 had much lower intracellular $p16^{INK4A}$ protein level than vehicle-treated NHEK.

From the above results, it can be found that all-trans retinoic acid continuously maintains telomerase activity in NHEK and decreases intracellular $p16^{INK4A}$ protein level, thereby, the all-trans retinoic acid according to the present invention can inhibit replicative senescence.

Accordingly, the inhibitor containing all-trans retinoic acid maintains telomerase activity in spite of continuous proliferation and in bits $p16^{INK4A}$ protein level in both NHOK and NHEK, thereby preventing replicative senescence of NHOK and NHEK. Therefore, the inhibitor containing all-trans retinoic acid as active ingredients can be used for a prophylactic or therapeutic agent of various diseases attributed to senescence of the human keratinocytes. In particular, the inhibitor containing all-trans retinoic acid as active ingredients can be used for a cosmetic purpose based on the result; the composite of all-trans retinoic acid enhances cell proliferation of NHEK and then inhibits replicative senescence for skin.

EXPERIMENTAL EXAMPLE 1

The Acute Oral Toxicity Test of Rat

To investigate the acute oral Toxicity test: Sprague-Dawley rats aged 6 weeks are used. Two rats per group were orally administered with all-trans retinoic acid and the 0.5% methyl cellulose solutions at a dose of 1 g/kg/15 ml one time. After administration, clinical symptoms, occurrence of death and the change of weight were observed. In addition, the rats were killed after administration, dissected, and celiac intestine and thoracic were examined with the unaided eye. Based on daily weight changes, blood test, blood biological test and opinion of autopsy, there were observed no toxicity.

As a result, $LD_{50}$ values of retinoic acid were found to be 2 g/kg above, which was very stable for toxicity.

PREPARATION EXAMPLE 1

Preparation of Syrup

A syrup containing 2% (weight/volume) of retinoic acid of the present invention as an active ingredient was prepared by the following procedure.

Acid addition salt of retinoic acid, saccharine, and sugar were dissolved in 80 g of warm water. The solution was cooled and then mixed with a solution comprising glycerin, saccharine, flavor, ethanol, sorbic acid, and distilled water. The reaction solution was added with water to a volume of 100 ml. The addition salt can be replaced with the other salts.

The composition of syrup above is as followed

| | |
|---|---|
| Acid addition salt of retinoic acid | 2.0 g |
| Saccharine | 0.8 g |
| Sugar | 25 4 g |
| Glycerin | 8.0 g |
| Flavour | 0.04 g |
| Ethanol | 4.0 g |
| Sorbic acid | 0.4 g |
| Distilled water | quantitative |

PREPARATION EXAMPLE 2

Preparation of Tablet

A tablet containing 15 mg of active ingredient was prepared by the following procedure.

250 g of retinoic acid hydrochloric acid salt was mixed with 175.9 g of lactose, 180 g of potato starch, and 32 g of colloidal silica. This mixture was added with 10% gelatin solution, pulverized and passed through a net of 14 messes. After drying it, the powder was added with 160 g of potato starch, 50 g of talc and 5.0 g of magnesium stearic acid to make a tablet.

The composition of tablet above is as followed.

| | |
|---|---|
| retinoic acid · hydrochloric acid salt | 250 g |
| potato starch | 175.9 g |
| colloidal silica | 32 g |
| 10% gelatin solution | |
| potato starch | 160 g |
| talc | 50 g |
| magnesium stearic acid | 5.0 g |

PREPARATION EXAMPLE 3

Preparation of Injectable Solution

An injectable solution containing 10 mg of active ingredient was prepared by the following procedure.

1 g of retinoic acid hydrochloric acid sale, 0.6 g of sodium chloride and 0.1 g of ascorbic acid were dissolved in distilled water to a volume of 100 ml. The solution was introduced into a vessel, heated for 30 minutes at 20° C. and sterilized.

The composition of an injectable solution above is as followed.

| | |
|---|---|
| retinoic acid · hydrochloric acid salt | 1.0 g |
| sodium chloride | 0.6 g |
| ascorbic acid | 0.1 g |
| distilled water | quantitative |

PREPARATION EXAMPLE 4

Preparation of Cream

A cream containing 10 mg of active ingredient was prepared by the following procedure.

The cream is prepared that 10 g of retinoic acid hydrochloric acid salt and the composition as below were dissolved in distilled water to a volume of 100 ml.

The composition of a cream is as followed.

| | |
|---|---|
| retinoic acid · hydrochloric acid salt | 10 g |
| cyclosiloxane | 24 g |
| scualrene | 5.0 g |
| lanoline | 3.0 g |
| fine crystallized wax | 3.0 g |
| propyleneglycol | 5.0 g |
| citric acid | 0.8 g |

-continued

| | |
|---|---|
| an antiseptic | 0.2 g |
| an aromatic | 1.0 g |
| polyoxyethylene stearyl ether | 3.0 g |
| distilled water | quantitative |

As described above, the retinoic acid in the present invention can not only extend the in vitro life span of the human oral mucosal keratinocytes and the human epidermal keratinocytes, but also inhibit the replicative senescence of the cells, thereby being used for a prophylactic or therapeutic agent various diseases such as trauma-caused inflammation, exelcymosis-caused inflammation, burn-caused inflammation, traumatic ulcer, and angular cheilosis, caused by senescence of the human oral mucosal keratinocytes In addition, the inhibitor containing all-trans retinoic acid of the present invention can inhibit against skin senescence and thus be used for a cosmetic purpose, and can be used for a prophylactic or therapeutic agent for wound-caused dermatitis and skin senescence.

The present invention has been described in an illustrated manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preventing replicative senescence of normal human skin, comprising:

(a) applying to normal human skin a composition consisting essentially of all-trans retinoic acid and a carrier;

(b) maintaining telomerase activity of normal human epidermal keratinocytes of the normal human skin and decreasing intracellular p16$^{INK4A}$ protein levels thereof.

2. A method for preventing replicative senescence of normal human epidermal keratinocytes that comprises contacting normal human keratinocytes with a composition consisting essentially of all-trans retinoic acid, and a carrier; in an amount effective to maintain telomerase activity of the normal human epidermal keratinocytes and to decrease intracellular p16$^{INK4A}$ protein levels thereof.

3. The method of claim 2, wherein the normal human keratinocytes are present in vivo.

* * * * *